US005540665A

United States Patent [19]
Mercado et al.

[11] Patent Number: 5,540,665
[45] Date of Patent: Jul. 30, 1996

[54] GAS DRIVEN DISPENSING DEVICE AND GAS GENERATING ENGINE THEREFOR

[75] Inventors: Stanley A. Mercado, Fremont, Calif.; Mark M. McPhee, Austin, Tex.; Avtar S. Nat, Fremont, Calif.; Su I. Yum, Los Altos, Calif.; Scott A. Bura, San Jose, Calif.

[73] Assignee: ALZA Corporation, Palo Alto, Calif.

[21] Appl. No.: 189,473

[22] Filed: Jan. 31, 1994

[51] Int. Cl.$^6$ ................................................ A61M 1/00
[52] U.S. Cl. ..................................... 604/145; 604/892.1
[58] Field of Search ............................ 604/890.1, 891.1, 604/892.1, 49, 54, 93, 131, 140, 145, 82, 83, 85

[56] References Cited

U.S. PATENT DOCUMENTS

| | | | |
|---|---|---|---|
| 2,674,619 | 4/1954 | Lundsted | 260/485 |
| 2,799,241 | 7/1957 | Wurster | 118/24 |
| 3,133,132 | 5/1964 | Loeb et al. | 264/49 |
| 3,173,876 | 3/1965 | Zobrist | 252/137 |
| 3,276,586 | 10/1966 | Rosaen | 210/90 |
| 3,325,357 | 6/1967 | Irani | 167/57 |
| 3,340,309 | 9/1967 | Weipert | 260/615 |
| 3,367,545 | 2/1968 | Cook | 222/389 |
| 3,504,041 | 3/1970 | Weipert | 260/615 |

(List continued on next page.)

FOREIGN PATENT DOCUMENTS

| | | | |
|---|---|---|---|
| 2159523 | 6/1973 | France | 604/145 |
| 2721752 | 11/1978 | Germany. | |

OTHER PUBLICATIONS

Vandercar, D. H., *Instrumentation & Techniques: An inexpensive infusion pump suitable for chronic administration of liquids to restrained or unrestrained animals*, 8 Behavior Research Methods & Instrumentation 487–488 (1976).

"Modern Plastics Encyclopedia," vol. 46, pp. 62 to 70, 1969.
"Remington's Pharmaceutical Science," 14th Ed., pp. 1649 to 1680, 1970, published by Mack Publishing Co., Easton, Pa.
"The Theory and Practice of Industrial Pharmacy," by Lachman, et al, pp. 197 to 225, 1970 published by Lea & Febiger, Philadelphia, Pa.
"Solubilization by Surface–Active Agents," by Elworth, P. H., et al, 1968, published by Chapman and Hall Ltd., London.
"Systemic Analysis of Surface–Active Agents," by Rosen, Milton J., et al. 1972, published by Wiley–Interscience Inc., Sydney.
"Encyclopedia of Polymer Science and Technology," vol. 13, pp. 477 to 486, 1970, published by John Wiley & Sons Inc., New York.
"J. of Am. Pharmaceutical Assn.," vol. 48, pp. 451–454 (1959).
"J. of Am. Pharmaceutical Assn.," vol. 49, pp. 82–84 (1960).
"Cosmeticology," by R. G. Harr, Chemical Publishing Co., New York, pp. 243–251.
"The Theory and Practice of Industrial Pharmacy," by Lachman, et al. pp. 618 to 621, 1970 published by Lea & Febiger, Philadelphia, Pa.

*Primary Examiner*—John D. Yasko
*Attorney, Agent, or Firm*—Richard T. Ito; Steven F. Stone; Mary Ann Dillahunty

[57] ABSTRACT

The present invention provides a gas generating engine for driving a beneficial agent dispensing device. The engine comprising (a) a solid composition comprising an acidic compound or a basic compound, or a combination thereof, and (b) a means for maintaining substantially constant the surface area of the solid composition exposed to a reservoir fluid comprising water, or water and an acidic compound, or water and a basic compound, wherein in operation, the solid composition is exposed to the reservoir fluid which dissolves the solid composition and causes it to generate a gas, the gas being a driving fluid to dispense a beneficial agent. The present invention further provides a fluid driven dispensing device for delivering an agent into an environment of use, the device be driven by the gas generating engine.

43 Claims, 6 Drawing Sheets

U.S. PATENT DOCUMENTS

| | | | |
|---|---|---|---|
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,604,417 | 9/1971 | Stolzenberg et al. | 128/213 |
| 3,732,865 | 5/1973 | Higuchi et al. | 128/260 |
| 3,760,804 | 9/1973 | Higuchi et al. | 128/260 |
| 3,760,984 | 9/1973 | Theeuwes | 222/95 |
| 3,796,817 | 3/1974 | Aepli et al. | 426/287 |
| 3,845,770 | 11/1974 | Theeuwes et al. | 128/260 |
| 3,867,938 | 2/1975 | Radcliffe | 604/145 |
| 3,946,734 | 3/1976 | Dedrick et al. | 551/120 |
| 3,971,376 | 7/1976 | Wichterle | 128/260 |
| 3,987,790 | 10/1976 | Eckenhoff et al. | 128/260 |
| 3,995,631 | 12/1976 | Higuchi et al. | 291/686 |
| 3,995,632 | 12/1976 | Nakano et al. | 128/260 |
| 4,008,719 | 2/1977 | Theeuwes et al. | 128/260 |
| 4,014,334 | 3/1977 | Theeuwes et al. | 654/194 |
| 4,036,228 | 7/1977 | Theeuwes | 128/260 |
| 4,217,894 | 8/1980 | Franetzki | 128/213 R |
| 4,320,758 | 3/1982 | Eckenhoff et al. | 128/260 |
| 4,327,725 | 5/1982 | Cortese et al. | 128/260 |
| 4,410,328 | 10/1983 | Theeuwes | 604/892 |
| 4,468,220 | 8/1984 | Willbanks | 604/133 |
| 4,474,575 | 10/1984 | Eckenhoff et al. | 604/131 |
| 4,511,355 | 4/1985 | Franetzki et al. | 604/131 |
| 4,539,004 | 9/1985 | Eckenhoff et al. | 604/131 |
| 4,576,604 | 3/1986 | Guittard et al. | 604/890 |
| 4,595,583 | 6/1986 | Eckenhoff et al. | 424/15 |
| 4,723,958 | 2/1988 | Pope et al. | 604/890.1 |
| 4,741,737 | 5/1988 | Meyer et al. | 604/140 |
| 4,773,900 | 9/1988 | Cochran | 604/143 |
| 4,838,862 | 6/1989 | Baker et al. | 604/892 |
| 4,846,801 | 7/1989 | Okuda et al. | 604/218 |
| 4,874,388 | 10/1989 | Wong et al. | 604/891 |
| 4,929,233 | 5/1990 | Roth et al. | 604/131 |
| 4,929,884 | 11/1990 | Yum et al. | 604/892.1 |
| 5,030,216 | 7/1991 | Theeuwes et al. | 604/892.1 |
| 5,151,093 | 9/1992 | Theeuwes et al. | 604/892.1 |
| 5,209,746 | 5/1993 | Balaban et al. | 604/892.1 |
| 5,234,424 | 8/1993 | Yum et al. | 604/892.1 |
| 5,279,608 | 1/1994 | Cheikh | 604/892.1 |
| 5,312,389 | 5/1994 | Theeuwes et al. | 604/892.1 |
| 5,312,390 | 5/1994 | Wong | 604/892.1 |

GAS DRIVEN DISPENSING DEVICE AND GAS GENERATING ENGINE THEREFOR

TECHNICAL FIELD

This invention pertains to a gas driven dispensing device for delivering a beneficial agent to an environment of use, and a gas generating engine therefor.

BACKGROUND ART

Over the past decade, much research has been devoted to developing new and useful devices for delivering beneficial agents to agent receptor environments of use. The traditional manner of administering sustained parenteral treatments is an intravenous drip. While this may be perfectly acceptable in a hospital environment, it is obviously imposes severe restrictions on the activity of the recipient. As a result, considerable research over the last few years has been devoted to the development of small portable infusion pumps.

A range of devices has appeared, including those with electric motors that drive pumps, and others powered by an osmotic engine. While these delivery techniques are being used, they have certain disadvantages. For example, the use of electromechanical pumps is expensive and sometimes inconvenient because of their size and weight. The use of an osmotic pumps, while small in size and requiring few moving parts, is slow in start-up time.

SUMMARY OF THE INVENTION

The present invention provides a gas generating engine for driving a beneficial agent dispensing device. In comparison with other driving mechanisms, a gas generating engine is quick-starting, small, reliable, uncomplicated and inexpensive to manufacture. The engine comprising (a) a solid composition comprising an acidic compound, or a basic compound, or a combination thereof, and (b) a means for maintaining substantially constant the surface area of the solid composition exposed to a reservoir fluid, wherein in operation, the solid composition is exposed to the reservoir fluid that comprises water, or water and an acidic compound, or water and a basic compound, which dissolves the solid composition and causes it to generate a gas, the gas being a driving fluid to dispense a beneficial agent.

The present invention further provides a fluid driven dispensing device for delivering an agent into an environment of use, the device comprising (a) a syringe having a moveable piston, the piston dividing the syringe into a beneficial agent compartment and a driving compartment; (b) a reservoir fluid comprising water, or water and an acidic compound, or water and a basic compound; and (c) a gas generating engine disposed within the driving compartment, the gas generating engine comprising: (i) a solid composition comprising an acidic compound, or a basic compound, or a combination thereof, and (ii) a means for maintaining substantially constant the surface area of the solid composition exposed to the reservoir fluid; wherein in operation, a beneficial agent is delivered from the device by the gas generating engine which is exposed to the reservoir fluid, the reservoir fluid dissolving the solid composition of the gas generating engine and causing it to generate a gas in the driving compartment, the gas exerting pressure on the piston to deliver the beneficial agent from the beneficial compartment to the environment of use.

In another embodiment, the fluid driven dispensing device comprises: a) housing means; b) piston means slidably received within the housing means, the piston means having first and second ends, the first end having a cross-sectional area greater than the second end; c) a beneficial agent compartment formed between the housing means and the first end of the piston means; d) a driving compartment formed between the housing means and the second end of the piston means; e) a reservoir fluid comprising water, or water and an acidic compound, or water and a basic compound; and f) a gas generating engine within the driving compartment actuatable by the reservoir fluid, the gas generating engine comprising: (i) a solid composition comprising an acidic compound, or a basic compound, or a combination thereof, and (ii) a means for maintaining substantially constant the surface area of the solid composition exposed to the reservoir fluid;
whereby a given volume of gas delivered to the driving compartment from the engine means will dispense a larger volume of beneficial agent from the beneficial agent compartment.

The present invention also provides a fluid driven dispensing device comprising: a) piston means having first and second ends, where the cross-sectional area of the first end of the piston is at least 1.5 times the cross-sectional area of the second end; and b) housing means slidably receiving the piston means, the first end of the housing forming an agent dispensing compartment having outlet means through which an agent may be displaced by movement of the first end of the piston, the second end of the housing being adapted to maintain a gas generating engine in discharging relationship to the second end of the piston and to contain a reservoir fluid for the engine, the improvement wherein the reservoir fluid comprises water, or water and basic compound, or water and acidic compound, and the gas generating engine comprises: (i) a solid composition comprising an acidic compound, or a basic compound, or a combination thereof, and (ii) a means for maintaining substantially constant the surface area of the solid composition exposed to the reservoir fluid.

The present invention includes a fluid driven dispensing device for delivering an agent into an environment of use, the device comprising a) housing means; b) piston means slidably received within the housing means, the piston means having first and second ends, the first end having a cross-sectional area greater than the second end; c) a beneficial agent compartment formed between the housing means and the first end of the piston means; d) a driving compartment formed between the housing means and the second end of the piston means; e) a reservoir fluid comprising water, or water and an acidic compound, or water and a basic compound; and f) a gas generating engine actuate by the reservoir fluid and in communicating relationship with the piston means, the gas generating engine comprising: (i) a solid composition comprising an acidic compound, or a basic compound, or a combination thereof, and (ii) a means for maintaining substantially constant the surface area of the solid composition exposed to the reservoir fluid; whereby a given volume of gas delivered to the driving compartment from the engine means will dispense a larger volume of beneficial agent from the beneficial agent compartment.

Preferably, in the device of this invention the area of the first end of the piston is at least 1.5 times greater than the area of the second end. More preferably, the area of the first end of the piston is between 3 and 10 times greater than the area of said second end.

Most preferably, the fluid driven dispensing device for delivering a beneficial agent to an environment of use comprises: a) a syringe housing adapted to contain the agent and having outlet means proximate one end thereof; b) an amplification housing attached at one end to the other end of the syringe housing; c) a driving housing attached to the other end of the amplification housing adapted to contain a reservoir fluid; d) piston means slidably received within the syringe housing and the amplification housing, the end of the piston means within the syringe housing comprising plunger means having a larger cross-sectional area than the end of the piston proximate the driving housing, the piston means being movable from a first position proximate the amplification housing end of the syringe housing to a second position proximate the outlet means; e) a reservoir fluid comprising water, or water and an acidic compound, or water and a basic compound disposed within the driving housing; and f) a gas generating engine actuatable by the reservoir fluid and in communicating relationship with the piston means, the gas generating engine comprising: (i) a solid composition comprising an acidic compound, or a basic compound, or a combination thereof, and (ii) a means for maintaining substantially constant the surface area of the solid composition exposed to the reservoir fluid; whereby a given volume of gas delivered to the piston means from the gas generating engine will dispense a larger volume of a beneficial agent from the syringe housing.

In operation, a beneficial agent is delivered from the device in the following manner. Gas is pumped into the driving compartment by the gas generating engine. Initially, the driving compartment has a small volume. The delivered gas exerts pressure on the second end of the piston means, the piston means moves within the housing, increasing the volume of the driving compartment. The movement simultaneously decreases the volume of the beneficial agent compartment, forcing the beneficial agent from the compartment and delivering it to the environment of use.

PIG. 3 is a cross-sectional view of another embodiment of a gas driven dispensing device of the present invention.

Figure 4:
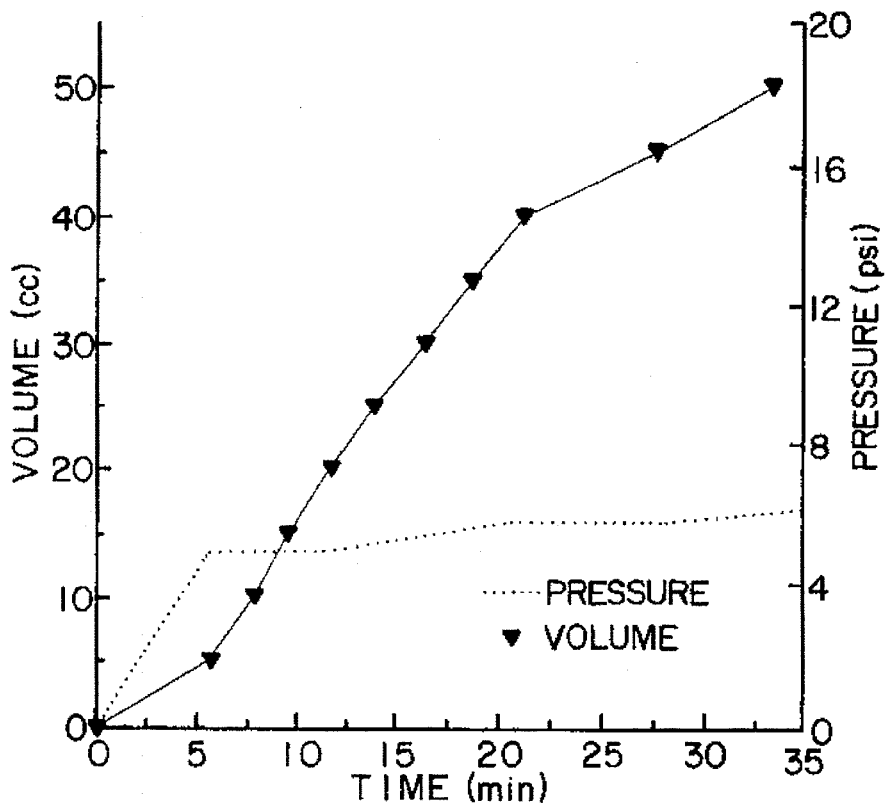

FIG. 4 is a graph of the pressure generated by the gas generating engine and the volume of beneficial agent displaced by the dispensing device over time.

Figure 5:
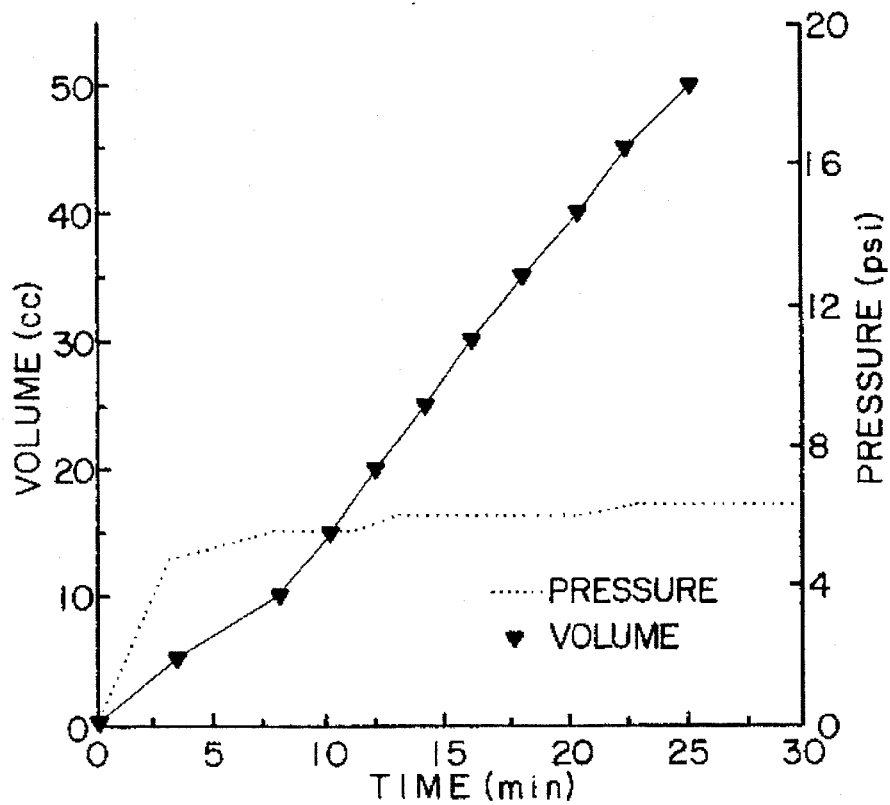

FIG. 5 is a graph of the pressure generated by the gas generating engine and the volume of beneficial agent displaced by the dispensing device over time.

Figure 6:
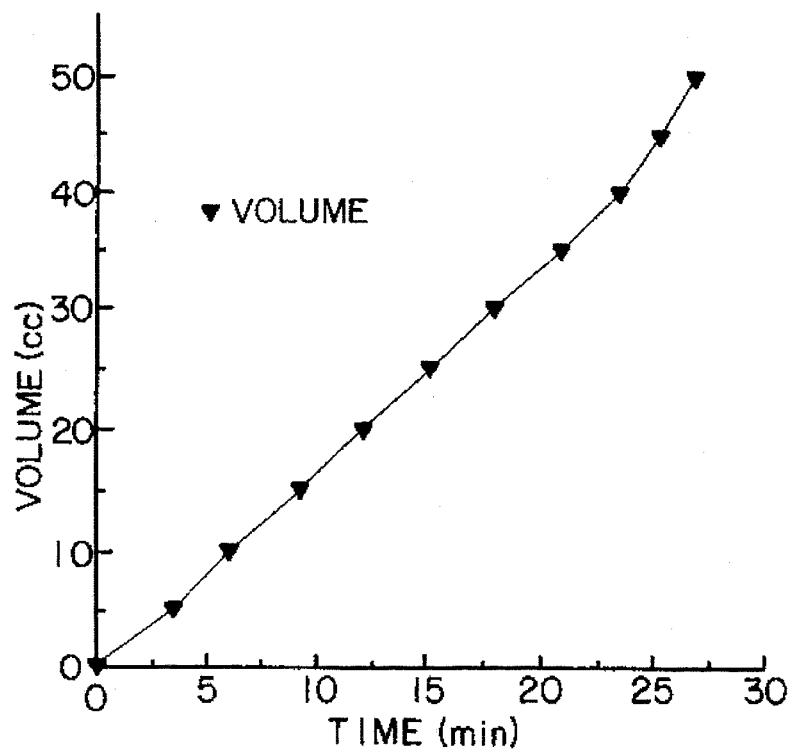

FIG. 6 is a graph of the volume of beneficial agent displaced by the dispensing device over time.

Figure 7:
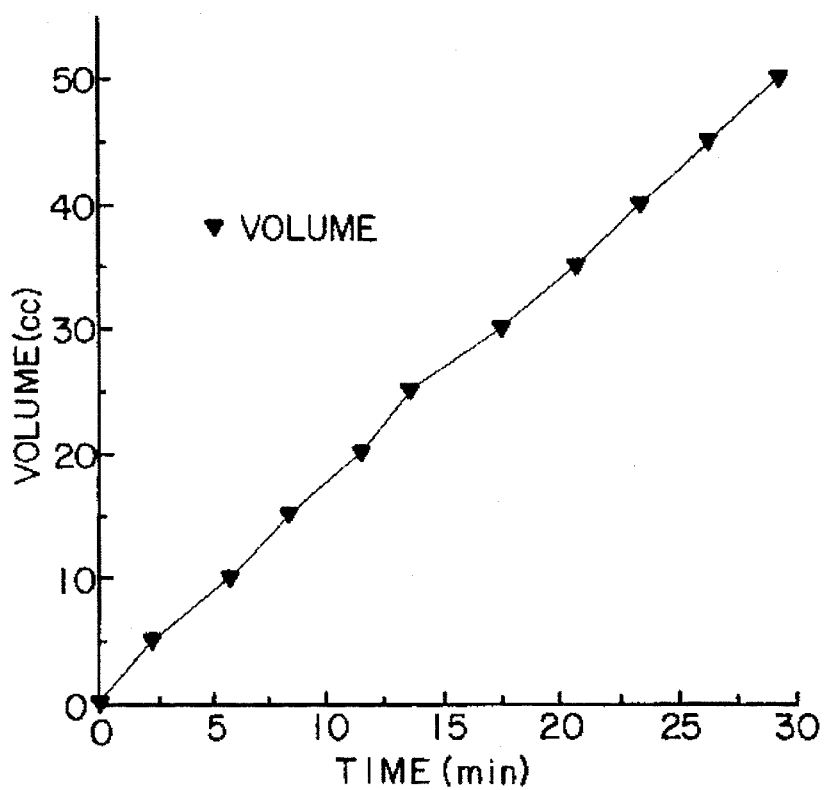
Figure 8:
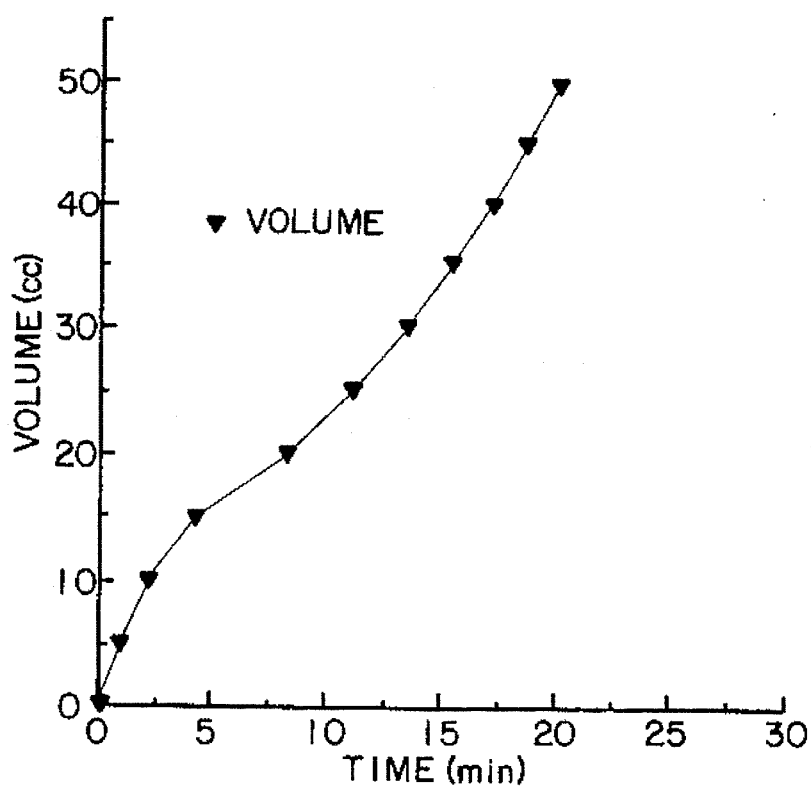
Figure 9:
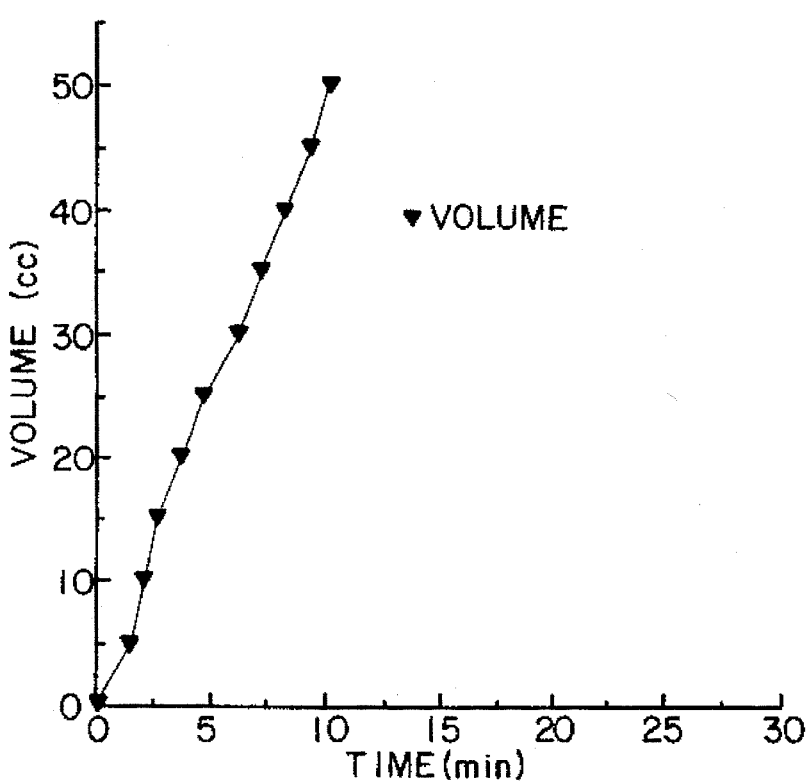

FIGS. 7, 8 and 9 are graphs of the volume of beneficial agent displaced by the dispensing device in different orientations over time.

Figure 10:
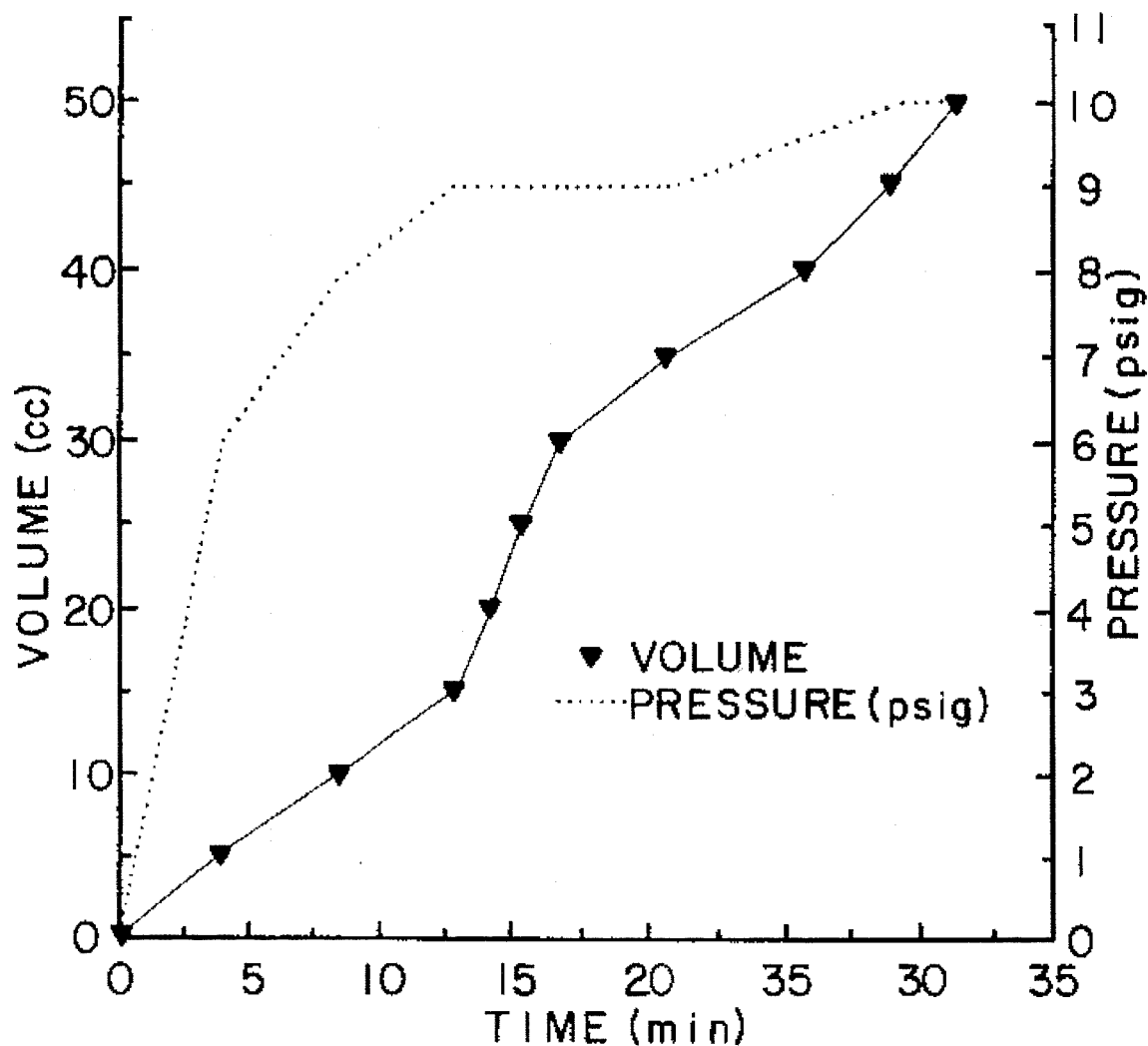

FIG. 10 is a graph of the pressure generated by the gas generating engine and the volume of beneficial agent displaced by the dispensing device over time.

MODES FOR CARRYING OUT THE INVENTION

Figure 1:
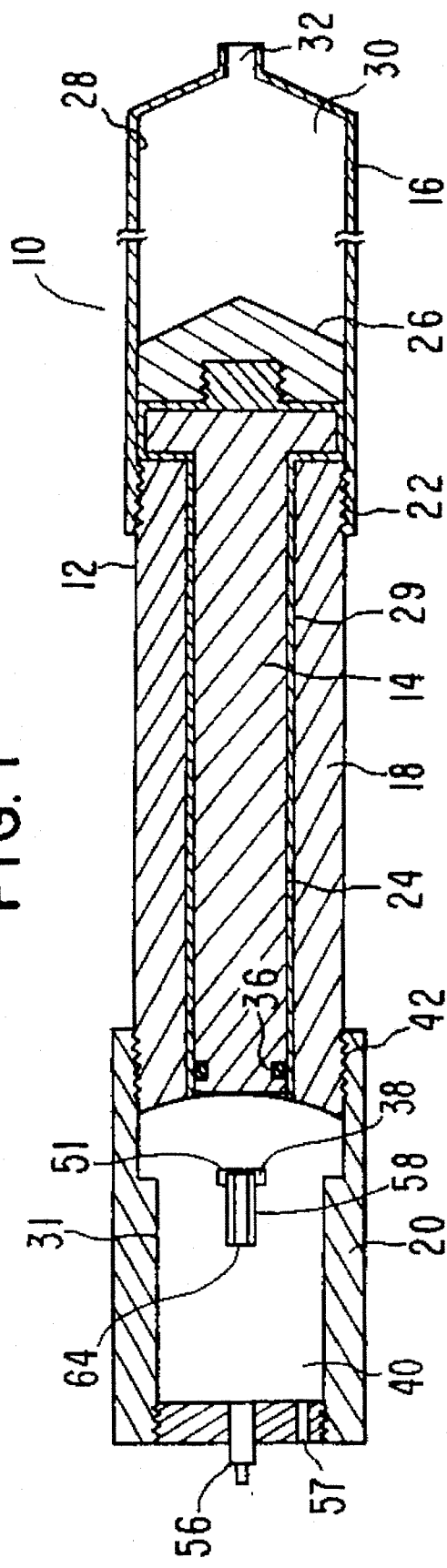
FIG. 1 is a cross-sectional view of a gas driven dispensing device of the present invention.
Figure 2:
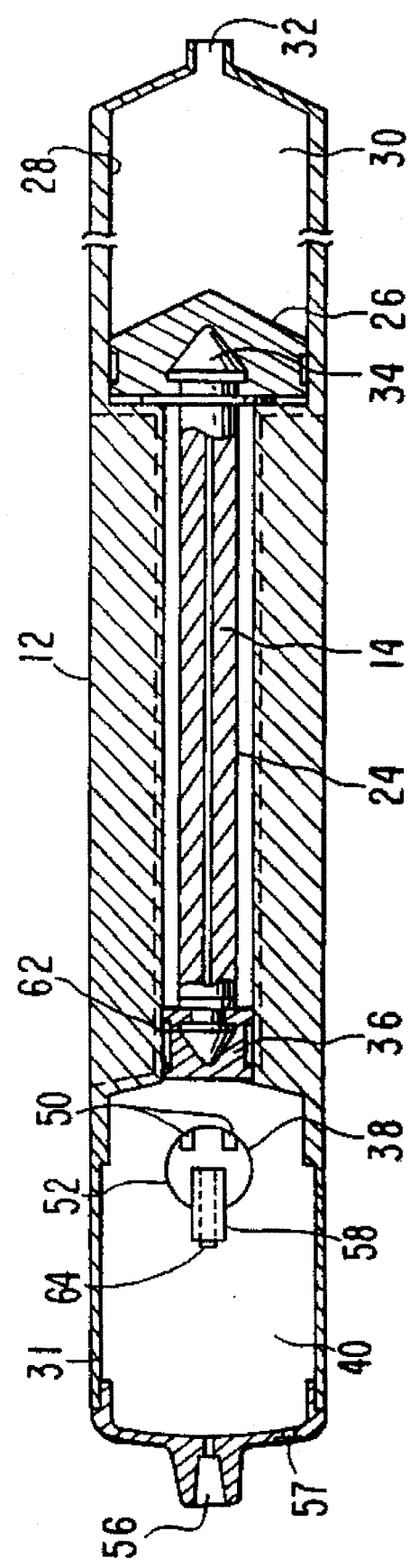
FIG. 2 is a cross-sectional view of another embodiment of a gas driven dispensing device of the present invention.

FIG. 1 is an opened, sectional view of a gas driven dispensing device depicting its internal structure. In FIG. 1, a device 10 comprises a housing 12 containing a movable plunger 26 disposed in contacting arrangement with one end of a moveable piston 14. In another embodiment of this invention, plunger 26 and piston 14 can be releasably attached or fixedly attached. Housing 12 comprises three separate sub-housings, a syringe housing 16, an amplification housing 18 and a driving housing 20.

Internal surface 28 of syringe housing 16 and plunger 26 define a beneficial agent compartment 30. Plunger 26 fits snugly against internal surface 28 of syringe housing 16 and is slidably movable along the internal surface 28, such that the volume of beneficial agent compartment 30 changes as plunger 26 moves. Agent compartment 30 has a delivery port 32 that can be shaped to accept a hypodermic needle, an IV catheter, or the like. Port 32 can also be adapted to accept a luer plug that is removed prior to connection with a hypodermic needle or IV catheter.

Syringe housing 16 is adapted to be fixedly attached to amplification housing 18 with a suitable fastening means 22, such as screw threads. Internal surface 29 of amplification housing 18 surrounds piston 14. Plunger 26 is disposed in contacting arrangement with the one end of piston 14. Piston 14 is slidably movable along internal surface 29 of amplification housing 18. In this embodiment, the cross-sectional area of piston 14 is smaller than the cross-sectional area of plunger 26. Optionally, the piston 14 and plunger 26 can have the same cross-sectional area.

Piston 14 comprises a rod 24 and a seal 36. Seal 36 on rod 24 provides fluid tight seal between seal 36 and the internal surface 29 of amplification housing 18. Preferably, the amount of friction between internal surface 29 and rod 24 is kept at a minimum. The internal surface 29 of amplification housing 18, seal 36, the end of piston 14 and internal surface 31 of driving compartment 20 define a driving compartment 40. The volume of driving compartment 40 changes as piston 14 moves. Optionally, the piston can be telescoping, such that an inner piston telescopes from an outer piston. This can be used to shorten the length of the device.

Gas generating engine 38 is disposed within driving compartment 40. The gas generating engine 38 includes a means for maintaining substantially constant the surface area of the solid composition exposed to the reservoir fluid. In this embodiment, the means is a shaped wall defining to tube 58. The tube 58 contains a solid composition 64 comprising an acidic compound or a basic compound, or a combination thereof. The tube 58 is comprised of a material that is impermeable to the reservoir fluid. The tube 58 is sealed on end with a plug 52.

Amplification housing 18 is adapted to be fixedly attached to driving Housing 20. In this regard, amplification housing 18 and driving housing 20 are provided with suitable fastening means 42, such as screw threads. Reservoir fluid is added to driving compartment 40 through port 56.

FIG. 2 depicts another embodiment of a fluid driven dispensing device. This embodiment is the same as described in FIG. 2, except for the features hereafter described. In this embodiment, housing 12 is one continuous housing and is not separable into three different sub-housings. Piston 14 and plunger 26 are provided with suitable fastening means 34, such as snap connects. Rod 24 and seal 36 are provided with suitable fastening means 62, such as snap connects.

Gas generating engine 38 is contained in driving compartment 40. The engine 38 comprises solid gas generating composition 64 partially contained in tube 58. The means for maintaining substantially constant the surface area of the solid composition exposed to the reservoir fluid comprises tube 58 surrounding composition 64. A self-righting means includes a spherical body 52 and weights 50 that maintain engine 38 in a vertical position regardless of the orientation of the device. The solid composition 64 in gas generating engine 38 protrudes from body 52. This allows for an initial burst of gas to fill the driving compartment 40. The size of the protrusion can be varied to increase or decrease the amount of the initial burst of gas.

Figure 3:
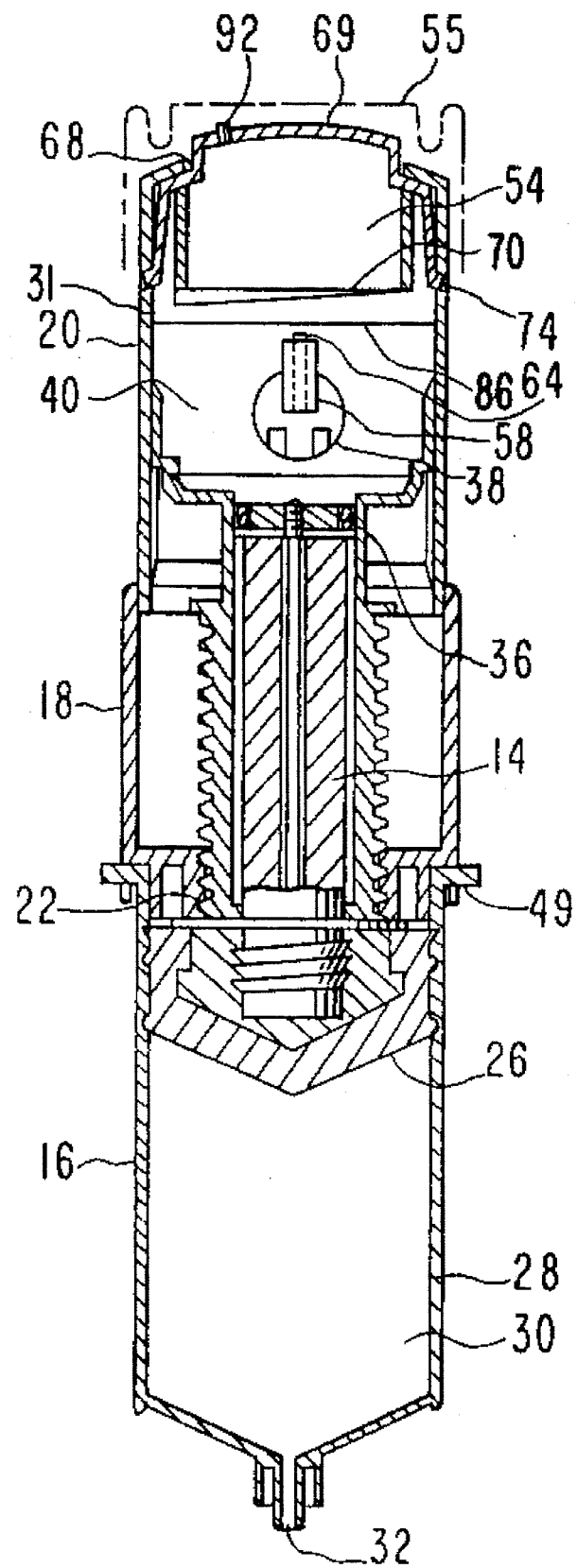

FIG. 3 represents the presently preferred embodiment of the fluid driven dispensing device. This embodiment is the same as FIG. 1, except for the features hereafter discussed. Syringe housing 16 is adapted to be movably attached to amplification housing 18 with a suitable fastening means 22, such as locking screw threads. When amplification housing 18 is attached to syringe housing 16, amplification housing 18 can be twisted to move piston 14 into contact with plunger 26 and allow chamber 40 to move relative housing 18. Further twisting decreases the volume of beneficial agent compartment 30 as plunger 26 moves, expelling any air trapped in beneficial agent compartment 30 when port 32 is pointed generally in an upward direction. A locking mechanism 49 can be employed to prevent amplification housing 18 from being further twisted after all trapped air has been removed.

The driving compartment 40 comprises interior 31 of the driving housing 20 and the end of piston 14. Within the driving compartment 40 is the gas generating engine 38, releasing means 70 and a breakable barrier 86. The breakable barrier 86 and the interior 31 of the driving compartment 40 form a reservoir compartment 54. Retention cap 68 is fixedly affixed to driving housing 20, by suitable fastening means 74, such as snap connects. The solid composition 64 in gas generating engine 38 protrudes from tube 58.

A protective cap 55 covers button 69 on retention cap 68. Pressing button 69 forces releasing means 70 to rupture barrier 86. Preferably releasing means 70 is an angled blade mounted on a support. Fluid from reservoir compartment 54 flows through releasing means 70 contacting engine 38. The releasing means can be located anywhere in the driving compartment.

In devices that are used to administer a drug intravenously, the pressure generated by the gas generating engine must exceed the patient's blood pressure. Sodium bicarbonate and citric acid are an especially effective combination in that the pressure generated is sufficient high. With the gas generating engine of this invention, the amount of gas generated is substantially constant, thus the rate of injection of the beneficial agent from agent compartment 30 is substantially constant. Such operation is called "steady state" or "tonic" operation and is characterized by a controlled constant rate of injection at predetermined baseline level.

In operation, reservoir fluid dissolves the gas generating composition, causing it to react and produce a large volume of gas. This gas expands into driving compartment 40. This action correspondingly causes pressure to be exerted on the piston 14 which thereby pushes this and the plunger 26, forcing beneficial agent into the environment of use through port 32.

Beneficial agent compartment 30 may be prefilled with a liquid dose of beneficial agent, or may be filled by the patient using a retracting device (not shown) which can be easily connected to plunger 26 for drawing the dose and which is easily disconnected from plunger 26 once the appropriate dose has been drawn.

In another embodiment of this invention, the driving compartment is defined by the retention cap, the piston and the driving housing. The driving compartment contains a releasing means that operates to puncture or rupture a reservoir fluid-filled reservoir compartment located inside the driving compartment. The reservoir compartment includes any rigid or non-rigid container that is impermeable to the reservoir fluid and can be ruptured or opened by the releasing means. Preferably, the container is a polymeric composition, such as high or low density polyethylene. The releasing means includes any means to open the barrier of the sealed container.

In another embodiment, the driving compartment is defined by the amplification housing of the device and surrounds the piston. The gas in the driving compartment communicates with the piston by a channel. A valve can be moved between a first or opened position where the gas communicates with the piston and second or closed position where the gas in the driving compartment is blocked from communicating with the piston. A valve that permits the gas to escape to the atmosphere is also present. The valve can either be manual or automatic, such that it releases at a pre-set pressure.

In yet another embodiment the driving compartment contains a microporous bag that is divided into two seal compartments. One compartment, the reservoir compartment, contains the reservoir fluid and the other compartment contains the gas generating engine. The seal between the two compartments is broken with a releasing means, thus bringing the reservoir fluid in contact with the gas generating engine. The microporous bag comprises a material that is permeable to the gas generated, but is impermeable to the reservoir fluid. Thus only the gas drives the piston, as the reservoir fluid is kept from contacting the piston. This makes the pump less sensitive to the orientation of the device.

Optionally, a one-way valve 57 can be placed on the driving compartment. The valve 57 can be opened and closed. In the closed position, the gas is confined to the driving compartment. In the open position, the gas can escape to the atmosphere. The opening and closing of valve 57 allows the delivery of beneficial agent to be stopped or interrupted at any time and to be restarted again, as long as the gas generating engine can generate gas. The valve 57 can also act as a safety valve, such that it releases at a preset pressure.

The solid composition of the gas generating engine comprises a solid compound or anhydrous mixture of compounds that when intimately contacted by the reservoir fluid, generates a gas that exerts a pressure to drive the dispensing system. The essentially dry or anhydrous composition comprises a solid acidic compound, or a solid basic compound, or a combination thereof, that dissolve and react in the presence of reservoir fluid. The composition may be in powder, crystalline, granular or layered form.

The acidic compounds that can be used include organic acids such as malic, fumaric, tartaric, itaconic, maleic, citric, adipic, succinic and mesaconic, and the corresponding anhydride such as itaconic anhydride, citriconic anhydride. Also inorganic acids such as sulfamic or phosphoric, and the like can be used for gas generation. Acid salts such as the salts of organic foods can be used including monosodium citrate, potassium acid tartrate and potassium bitartrate. Combinations of the above acidic compounds can also be used.

The basic compounds include metal carbonate and bicarbonate salts, such as alkali metal carbonates and bicarbonates, or alkaline earth carbonates and bicarbonates. Exemplary materials include the alkali metals lithium, sodium, potassium carbonate and bicarbonate, and the alkaline earth compounds magnesium and calcium carbonate or bicarbonate. Also useful are ammonium carbonate, ammonium bicarbonate and ammonium sesquecarbonate. Combinations of the above basic compounds can also be used.

The combination of certain of these acids and bases results in a more rapid gas production when contacted with water. In particular, a preferred combination is the solid composition comprising sodium bicarbonate with the reservoir fluid comprising water and citric acid. It will be understood the amount of acidic and basic compounds in a couple can vary over a wide range to satisfy the amount of gas generation needed to dispense beneficial agent from dispenser 10. The acidic and basic compounds are preferably substantially stoichiometrically balanced to produce a combination that generates carbon dioxide. Also, the acid and base compounds can be used in any convenient proportion between 1 to 200 parts and 200 to 1 part on a weight basis to produce the desired results. In addition, the gas generating composition can be a substance that generates gas on contact with water such as calcium carbide or carbure.

The solid composition can further comprise a water soluble, inorganic salt. Preferably, the solid composition comprises 50% to 95% acidic solid compound and basic solid compound, and 5% to 50% water soluble, inorganic salt. More preferably, the solid composition comprises 70% to 90% acidic solid compound and basic solid compound, and 10% to 30% water soluble, inorganic salt.

In a preferred embodiment of the gas generating engine, the solid composition comprises a basic solid compound and the reservoir fluid comprises water and an acidic compound. Preferably, the solid basic compound is $NaHCO_3$ and the acidic compound is $HO(CH_2COOH)_2COOH$.

In the most preferred embodiment, the solid basic composition comprises 90%–100% $NaHCO_3$, 0–10% polyvinyl pyrrolidone and 0–5% magnesium stearate and the reservoir fluid comprises water and 0.01%–10% $HO(CH_2COOH)_2COOH$.

The gas generating composition can also contain a foaming agent, such as a surfactant, having suitable foaming properties to stabilize the gas generated. The surfactant when mixed with the imbibed reservoir fluid and the gas produced by the gas generation composition, forms a foam. The surfactant can be cationic, anionic or nonionic. Exemplary cationic surfactants include, lauryldimethylbenzylammonium chloride p-di-isobutylphenoxyethoxyethyl-dimethylbenzylammonium chloride, alkyl-dimethylbenzylammonium chloride, laurylisoquinolinium bromide, cetylethyldimethylammonium bromide, stearyl-dimethylbenzylammonium chloride, N-soya-N-ethyl-morpholinium-ethosulphate, N(acyl-colaminoformyl-methyl)pyridinium chloride, a mixture comprising alkyl ($C_9H_{19}$ to $C_{15}H_{31}$)tolylmethyltrimethylammonium chloride and lauryl-isoquinolinium bromide, coco-amidoalkyl betaine, and N-lauryl-myristyl-β-aminopropionic acid.

Exemplary anionic surfactants include linear alkylaryl sulfonates prepared by Friedel-Crafts reaction of an olefin and benzene wherein the olefin has from 10 to 18 carbon atoms, and the alkali metal salts thereof, and other anionic surfactants such as alkylaryl sulphonate, capryl imidazoline derivatives, dioctylester of sodium sulphosuccinic acid, sodium lauryl sulfate, sodium salt of alkylated aryl polyether sulphate, triethanolamine salt of lauryl sulphate, triethanolamine salt of alkylaryl sulfonate; and mixtures thereof. Exemplary nonionic surfactants include alkylated aryl polyether alcohol, polyethylene glycol tertdodecyl thioether, fatty acid amide condensates, aromatic polyglycol ether condensates, secondary amide of lauric acid, fatty acid alkanolamine condensates, sorbitan monolaurate, sorbitan monolaurate polyoxyethylene, sorbitan mono-oleate, sorbitan mono-oleate polyoxyethylene derivative, mannide mono-oleate polyoxyethylene lauryl ether, polyoxyethylene esters of mixed resins and fatty acids, and mixtures thereof, and surfactants generically including the condensation product of a linear aliphatic alcohol having from 8 to 22 carbon atoms in its aliphatic portion and an alkylene oxide wherein the oxide constitutes from about 55% to 80% by weight of the surfactant molecule.

The amount of surface active agent used is an amount sufficient to achieve the intended result, normally, the amount will range from 0.01% to about 15% by weight, based on the total weight of all the compounds in the engine. The surface active agents are commercially available and they are also known in *Solubilization By Surface-Active Agents,* by Elworthy; P. H., et al, 1968, published by Chapman and Hall Ltd., London; *Systemic Analysis of Surface-Active Agents,* by Rosen, Milton J., et al, 1972, published by Wiley-Interscience Inc., Sydney; *Encyclopedia of Polymer Science and Technology,* Vol. 13, pages 477 to 486, 1970, published by John Wiley & Sons Inc., New York; and U.S. Pat. Nos. 2,674,619, 3,340,309, 3,504,041, and 3,796,817.

Suitable foam forming agents which can be mixed with the gas generating composition for the above described purpose include those that produce a foam that is stable within a wide range of temperature, that produces a foam that does not collapse in the presence of other compounds, and produces a foam that is pharmaceutically acceptable when thee syringe dispenses a drug to an animal. Exemplary foam-formers are alkyl aryl sulphonates, sodium, ammonium and alkanolamine ether sulphates such as monoethanolamine lauryl ether sulphate and dodecyl benzene sulphonate, a mixture consisting of lauryl-amidopropyl-N-dimethylamino acetic acid and stearylamidopropyl-N-dimethylamino acetic acid, a mixture consisting of monoethanolamine lauryl ether sulphate and methyl cellulose in a weight ratio of 3:1, a foaming surfactant consisting of sodium alkyl benzene sulphonate in combination with lauryl sulphate and sodium lauryl sulphoacetate. The amount of foam-forming agent used usually is about 0.01% to 15% by weight based on the total weight of the compounds in the device. Representative foam-formers and foam systems are described in *The Theory and Practice of Industrial Pharmacy,* by Lachman, L. et al, pages 618 to 621, 1970, published by Lea & Febiger, Philadelphia; and in *Cosmeticology,* by Harry, R. G., pages 243 to 250, 1973, published by Chemical Publishing Co. Inc., New York.

In determining the amount of gas generating composition needed within the engine, the compressibility of the gas produced by the gas generating reaction must be taken into account. In a typical syringe, the pressures generated within driving compartment will be such that the volume of gas produced will be on the order of about 30% to 70% of the volume of the gas at standard atmospheric pressure. Those skilled in the art will appreciate that the compressibility of the gas produced is simply compensated for by adding from 70% to 30% more gas generating composition than would be required at standard atmospheric pressure.

The means for maintaining the surface area of the solid composition exposed to the reservoir fluid substantially constant can comprise a body having a rigid structure external to the solid composition. The structure can be any suitable means to provide a substantially constant surface area, such as a tubular structure, a rectangular structure or a spherical structure. The structure can be made of ceramic, metal, plastic or the like. Preferably, the structure surrounds at least 50% of the surface area of the solid composition, wherein in operation the structure maintains two of the three dimensions of the solid composition constant as the reservoir fluid dissolves the solid composition. Most preferably, the structure surrounds at least 80% of the solid composition and a portion of the composition protrudes from the structure to provide an initial burst of gas.

Preferably, the gas generating engine further comprises a self-righting means wherein the surface area of the solid composition exposed to the reservoir fluid faces in an upward direction regardless of the orientation of the device. More preferably, the self-righting means comprises one end of the tube being heavier than the other end of the tube, for example, wherein the self-righting means comprises an air bubble in one end of the tube, or a weighted body, particularly a weighted spherical ball.

The device of this invention can further comprise a collapsible enclosure means enclosing the reservoir fluid for the gas generating engine, the enclosure means being disposed within the driving housing; and a releasing means for puncturing the enclosure means; whereby the reservoir fluid may be released into the driving housing and into contact with the gas generating engine. The device can also further comprise means or the driving housing for placing the releasing means in puncturing relationship to the enclosure means.

The fluid driven dispensing devices of the present invention may be used to deliver dosages having a fluid volume in a range of about 0.5 ml to about 200 ml over a period of about 5 minutes to about 24 hours. The engines useful in the fluid driven dispensing devices disclosed herein typically provide a delivery rate of about 0.1 ml/hr to about 300 ml/hr.

The fluid driven dispensing device can optionally be made as a reusable device. That is the agent compartment can be refilled, the engine can be replaced, with another engine having the same or different pumping rate, and the reservoir can be refilled with reservoir fluid or pre-packaged reservoir fluid.

The housing for the device may be manufactured by injection or compression molding, vacuum forming or any standard technique for handling thermoplastic polymers, such as polyvinyl chloride, polymethylmethacrylate, polyethylene, polycarbonate, polysulfone or the like. Alternatively, the housing could be made from thin sheets of stainless steel, aluminum or like metal.

The assembled fluid driven dispensing device is placed on the skin with a needle (not shown) penetrating the cutaneous layer and lying substantially flush against the skin. Alternatively, the needle can be inserted into a vein and the syringe utilized as an IV infusion device. When the fluid driven syringe is used in combination with a subcutaneous or IV needle, the needle is preferably composed of stainless steel and has a gauge in the range of 25 to 30.

Alternatively, the fluid in compartment 54 may be inert and the device may be used simply as a displacement pump. In this alternative, the device will have to be suitably interconnected by well known means to a reservoir of a fluid beneficial agent to be discharged, such that the inert fluid displaces the beneficial agent from the reservoir in a predetermined regimen to the desired administration site.

The present invention can either be filled when its use is desired or can be filled and stored for extended periods of time and then activated on demand. Accordingly, the reservoir fluid to drive the gas generating engine can be either 1) added through sealed inlet means 56 to the driving compartment containing the gas generating engine, 2) released from a reservoir compartment by a releasing means into contact with the gas generating engine, wherein the gas generated enters the driving compartment, 3) released from a reservoir compartment by a releasing means into the driving compartment, or 4) released from a sealed portion of the driving compartment by a releasing means. The reservoir fluid dissolves the solid composition of the gas generating engine forming the driving gas. The releasing means may be a simple needle, a plurality of needles, a serrated support, a cutting blade and the like to tear or rip a sealed container or it may be a moving partition, such as lever, a gate, a plunger, a plug and the like to open a sealed container. It is intended that the scope of the present invention should encompass any releasing means.

The compartment containing the reservoir fluid should be completely impermeable to the fluid, otherwise slow migration of the fluid will cause the device to deteriorate during storage. The compartment can be made of high density polyethylene, polyvinyl chloride, acrylonitrile, stainless steel, aluminum or a like metal, or thermoplastic polymers, such as polyvinyl chloride, polymethylmethacrylate, polyethylene, polycarbonate, polysulfone, and the like.

As used herein, the term "substantial portion of the time period" means at least about 60% of the time period, preferably at least about 90% of the time period.

As used herein, the term "substantially constant" means a variation of less than ±20%, preferably less than ±10%, over a substantial portion of the time period.

The term "beneficial agent", as used herein, includes any agent or compound, that can be delivered from the device to produce a beneficial and useful result, including any physiologically (i.e., denotes the administration of a beneficial agent to produce normal levels or functions) or pharmacologically active substance (i.e, denotes variations in response to amount of beneficial agent administered to host) that produces a local or systemic effect when administered to an animal. In general, this includes beneficial agents in all of the major therapeutic areas including, but not limited to: ACE inhibitors, adenohypophyseal hormones, adrenergic neuron blocking agents, adrenocortical steroids, inhibitors of the biosynthesis of adrenocortical steroids, alpha-adrenergic agonists, alpha-adranergic antagonists, selective alpha-two-adrenergic agonists, analgesics, antipyretics and antiinflammatory agents, androgens, local anesthetics, general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholmines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opioid analgesics and antagonists, pancreatic enzymes, phenothiazines, polypeptides, progestins, prostaglandins, proteins, agents for the treatment of psychiatric disorders, retinoids, sodium channel blockers, agents for spasticity and acute muscle spasms, succinimides, thioxanthenes, thrombolytic agents, thyroid agents, tricyclic antidepressants, inhibitors of tubular transport of organic compounds, drugs affecting uterine motility, vasodilators, vitamins and the like.

Exemplary drugs that can be delivered by the devices of this invention, include alclometasone, aldosterone, amcinonide, beclomethasone dipropionate, betamethasone, clobetasol, clocortolone, cortisol,ortisone, corticosterone, desonide, desoximetasone, 11-desoycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6α-methylprednisolone, mometasone, paramethasone, prednisolone, prednisone, tetrahydrocortisol, triamcinolone, $\alpha_2$-antiplasmin, aminocaproic acid, plasminogen, streptokinase, urokinase, erythropoietin, ferrous fumarate, ferrous gluconate, ferrous sulfate, folic acid, interleukin-3, pyridoxine, thrombopoietin, vitamin $B_{12}$, alpha-ergocryptine, beta-ergocrytine, bromocriptine, dihydro-beta-ergocryptine, dihydroergotamine, dihydroergocristine, dihydroergocornine, elymoclavine, ergocornine, ergocristine, ergometrine, ergonovine, ergosine, ergotamine, ergotoxine, d-isolysergic acid, lergotrile, lisuride, d-lysergic acid, lysergol, metergoline, methylergonovine, methysergide, flufenamic acid, ibuprofen, mefenamic acid, naproxen, propranolol, tolfenamic acid, sumatriptan, amphotericin B, butoconazole, ciclopirox olamine, clotrimazole, econazole, fluconazole, flucytosine, griseofulvin, haloprogin, imidazole, iodide, itraconazole, ketoconazole, miconazole, naftifine, natamycin, nystatin, oxiconazole, sulconazole, terconazole, tolnaftate, undecylenic acid, ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, danazol, fluoxymesterone, methandrostenolone, methyltestosterone, nandrolone decanoate, nandrolone phenpropionate, oxandrolone, oxymetholone, stanozolol, testolatone, testosterone, testosterone cypionate, testosterone enanthate, testosterone propionate, chlorotrianisene, diethylstilbestrol, estradiol, estradiol cypionate, estradiol valerate, estrone, estrone sodium sulfate, estropipate, ethinyl estradiol, mestranol, quinestrol, sodium equilin sulfate, acetaminophen, allopurinol, apazone, auranofin, aurothioglucose, colchicine, diclofenac, diflunisal, etodolac, fenoprofen, flurbiprofen, gold sodium thiomalate, indomethacin, ketoprofen, ketorolac, meclofenamate, mesalamine, methyl salicylate, nabumetone, oxyphenbutazone, phenacetin, phenylbutazone, piroxicam, salicylamide, salicylic acid, salsalate, sulfasalazine, sulindac, tolmetin, alfentanil, chloroform, clonidine, diazepam, diethyl ether, droperidol, etomidate, fentanyl, ketamine hydrochloride, lorazepam, meperidine, methohexital, midazolam, morphine, propofol, sufentanil, thiamylal, thiopental, acetohexamide, buformin, chlorpropamide, ciglitazone, diazoxide, gliclazide, glipizide, glucagon, glyburide, insulin, metformin, somatostatin, tolazamide, tolbutamide, cisapride, chlorpromazine, domperidone, dronabinol, haloperidol, metoclopramide, nabilone, perphenazine, prochlorperazine, promethazine, thiethylperazine, triflupromazine, trimethobenzamide, amikacin, aminoglycoside, aminosalicylic acid, ampicillin, amoxicillin, azlocillin, aztreonam, bacampicillin, bacitracin, capreomycin, carbenicillin, carbenicillin indanyl, cefaclor, cefadroxil, cefamandole, cefazolin, cefonicid, cefoperazone, ceforanide, cefotaxime, cefotetan, cefoxitin, ceftazidime, ceftriaxone, ceftizoxime, cefuroxime, cephalexin, cephalothin, cephapirin, cephradine, chloramphenicol, chlortetracycline, cinoxacin, ciprofloxacin, clavulanate, clindamycin, clofaziine, cloxacillin, colistin, cyclacillin, cycloserine, dapsone, demeclocycline, dicloxacillin, doxycycline, epicillin, ethambutol, ethionamide, erythromycin, gentamicin, imipenem, isoniazid, kanamycin, mafenide, methacycline, methenamine, methicillin, metronidazole, mezlocillin, minocycline, nafcillin, nalidixic acid, neomycin, netilmicin, nitrofurantoin, norfloxacin, oxacillin, oxytetracycline, penicillin G, penicillin V, pentamidine, piperacillin, pivampicillin, polymyxin B, probenecid, pyrazinamide, rifampin, silver sulfadiazine, spectinomycin, streptomycin, sulbactam, sulfacetamide, sulfacytine, sulfadiazine, sulfadoxine, sulfamethizole, sulfamethoxazole, sulfisoxazole, sulfonamide, sulfoxone, talampicillin, tetracycline, ticarcillin, tobramycin, trimethoprim, vancomycin, adenosine, aminoglutethimide, azaribine, azathioprine, azauridine, bleomycin, busulfan, carboplatin, carmustine, chlorambucil, cisplatin, cyclophosphamide, cytarabine, dacarbazine, dactinomycin, daunorubicin, doxorubicin, erythrohydroxynonyladenne, etoposide, floxuridine, fluorouracil, flutamide, hexamethylmelamine, hydroxyurea, ifosfamide, interferon alfa, l-asparaginase, leuprolide, lomustine, mechlorethamine, melphalan, mercaptopurine, methotrexate, mitomycin, mitotane, mitoxantrone, pentostatin, plicamycin, procarbazine, semustine, streptozocin, tamoxifen, taxol, teniposide, thioguanine, thiotepa, vinblastine, vincristine, benznidazole, chloroguanide, chloroquine, clioquinol, diethylcarbamazine, dehydroemetine, diloxanide furoate, emetine iodoquinol, ivermectin, mebendazole, mefloquine, melarsoprol, metrifonate, metronidazole, niclosamide, nifurtimox, oxamniquine, paromomycin, piperazine, praziquantel, primaquine, pyrantel pamoate, pyrimethamine, quinacrine, quinine, stibogluconate, suramin, tinidazole, thiabendazole, mecamylamine, procainamide, amphetamine sulfate, isoprotetrenol, methamphetamine, phenmetrazine, bethanechol chloride, methacholine chloride, atropine, methscopolamine bromide, isopropamide iodide, tiridihexethyl chloride, methylphenidate, oxprenolol, metoprolol, cimetidine, tretinoin, diphenidol, meclizine, phenoxybenzamine, digoxin, reserpine, acetazolamide, methazolamide, bendroflumethiazide, chlormadinone acetate, nitroglycerin, valproic acid, timolol, atenolol, imipramine, levodopa, methyl-dopa, theophylline, and the like. The beneficial drugs known in the art are listed in the 1993 USAN and USP dictionary of drug names, published by the United States Pharmacopeial Convention, Inc., Rockville, Md.

The beneficial agent can be in various forms, such as uncharged molecules, molecular complexes, pharmacologically acceptable salts such as hydrchloride, hydrobromides, sulfate, laurylate, palmitate, phosphate, nitrite, borate, acetate, maleate, tartrate, oleate, and salicylate. For acid drugs, salts of metals, amines or organic cations, for example, quaternary ammonium can be used. Derivatives of beneficial agents such as esters, ethers and amides can be used. Beneficial agents broadly includes any active substance for producing a localized effect at the administration site or a systemic effect at a site remote from the administration site.

Agents that can be dispensed by the fluid driven dispensing device include drugs, antibacterials, antifungals, plant growth promoters, surfactants, chemical reactants, and the like. The fluid driven dispensing device described herein is particularly useful for the long-term administration of pharmaceutical compositions such as insulin, analgesics, anti-nausea and anti-cancer drugs.

EXAMPLE 1

A gas generating engine containing 1% polyvinylpyrrolidone was made as follows: 57.28 g of sodium bicarbonate and 0.58 g of polyvinylpyrrolidone K29-32 (Union Carbide, Connecticut) were blended for 20 minutes. 3.0 ml of isopropyl alcohol was then added to the mixture. The mixture was passed through a 18 mesh screen, dried for 20 minutes at 50° C. and then passed through a 20 mesh screen. 55.98 g of material was recovered. To this composition was added 0.14 g of magnesium stearate. The solid composition was compressed into a tubular shaped tablet and then put into a high density polyethylene tube having a 0.375 inch inner diameter. The tube was sealed at one end.

A gas generating engine containing 2% polyvinylpyrrolidone was made as follows: 47.88 g of sodium bicarbonate and 1.00 g of polyvinylpyrrolidone K29-32 were blended for 20 minutes. 2.2 ml of isopropyl alcohol was then added to the mixture. The mixture was passed through a 20 mesh screen, dried for 20 minutes at 50° C. and then passed through a 20 mesh screen. 55.98 g of material was recovered. To this composition was added 0.12 g of magnesium stearate. The mixture was then put into a tube having an inner diameter of 0.375 inches. The tube was sealed at one end.

A reservoir fluid of 5%, 10% and 20% w/w was made of citric acid and water. The 5%, 10% and 20% reservoir fluid was formulated as followed: 11.06 g of citric acid in 209.99 g of water, 30.00 g of citric acid in 210.01 g of water and 60.00 g of citric acid in 240.02 g of water.

The gas generating engine was placed in the reservoir fluid. The disintegration resulted in the generation of carbon dioxide gas.

EXAMPLE 2

A gas generating engine was made as follows: 0.50 g of solid composition containing 25% NaCl and 75% acidic compound and basic compound in a one to one stoichiometric arrangement were compressed into a tubular shaped tablet and placed in a tube having an inner diameter of 0.172 and an outer diameter of 0.250. One end of the tube was sealed. The acidic compound was citric acid and the basic compound was sodium bicarbonate.

The gas generating engine was then placed in a beneficial agent dispensing device comprising a syringe housing adapted to contain the beneficial agent and having outlet means proximate one end thereof; an amplification housing attached at one end to the other end of the syringe housing; driving housing attached to the other end of the amplification housing adapted to contain a reservoir fluid and a gas generating engine and a piston means slidably received within the syringe housing and the amplification housing, the end of the piston means within the syringe housing comprising plunger means having a larger cross-sectional area than the end of the piston proximate the driving housing. The syringe portion of the device contained 140 cc of beneficial agent. The 30 cc of reservoir fluid was added to the device. The device was then placed in an incubator at 30° C. FIG. 4 shows the gas pressure generated by the gas generating engine and the volume of beneficial agent displaced by the device.

EXAMPLE 3

A gas generating engine was made as follows: 0.57 g of solid composition containing 25% NaCl and 75% acidic compound and basic compound in a one to one stoichiometric arrangement were compressed into a tubular shaped tablet and placed in a tube having an inner diameter of 0.172 and an outer diameter of 0.250. One end of the tube was sealed. The acidic compound was citric acid and the basic compound was sodium bicarbonate. The solid composition protruded from the tube 0.120 inches The gas generating engine was then placed in a beneficial agent dispensing device comprising a syringe housing adapted to contain the beneficial agent and having outlet means proximate one end thereof; an amplification housing attached at one end to the other end of the syringe housing; a driving housing attached to the other end of the amplification housing adapted to contain a reservoir fluid and a gas generating engine and a piston means slidably received within the syringe housing and the amplification housing, the end of the piston means within the syringe housing comprising plunger means having a larger cross-sectional area than the end of the piston proximate the driving housing. The syringe portion of the device contained 140 cc of beneficial agent. The 30 cc of reservoir fluid was added to the device. The device was then placed in an incubator at 30° C. FIG. 5 shows the gas pressure generated by the gas generating engine and the volume of beneficial agent displaced by the device.

EXAMPLE 4

A gas generating engine was made as follows: 0.45 g of solid composition containing 20% NaCl and 80% acidic compound and basic compound in a one to one stoichiometric arrangement were compressed into a tubular shaped tablet and placed in a tube having an inner diameter of 0.172 and an outer diameter of 0.250. One end of the tube was sealed. The acidic compound was citric acid and the basic compound was sodium bicarbonate. The composition filled 5/8 of an inch of the tube in length. On top of this composition was placed 0.29 g of solid composition containing 100% acidic compound and basic compound in a one to one stoichiometric arrangement. This composition was compressed into a tubular shaped tablet being 7/16 of an inch in length. The composition protruded from the tube 5/16 of an inch.

The gas generating engine was then placed in a beneficial agent dispensing device identical in description to that described in Example 4. The syringe portion of the device contained 140 cc of beneficial agent. The 25 cc of reservoir fluid was added to the device. The device was then placld in an incubator at 30° C. FIG. 6 shows the volume of beneficial agent displaced by the device.

EXAMPLE 5

A gas generating engine was made as follows: In an acrylic sphere, that was 3/4 inches in diameter, a 0.173 inch diameter and 0.720 inch length hole was bored in the center of the sphere. 0.70 g of solid composition containing 100% acidic compound and basic compound in a one to one stoichiometric arrangement were compressed into a tubular shaped tablet and placed in the hole. The composition protruded 0.25 inches from the sphere, The acidic compound was citric acid and the basic compound was sodium bicarbonate.

On the opposite side of the sphere in which the hole was bored for the solid composition, two additional holes were bored having a diameter of 0.125 and a length of 0.3 inches. In these holes were inserted two cylindrical lead weights.

The gas generating engine was then placed in a beneficial agent dispensing device identical to that described in Example 4. The syringe portion of the device contained 140 cc of beneficial agent. The 30 cc of reservoir fluid was added to the device. The device was tested at room temperature. FIGS. 7, 8 and 9 show the volume of beneficial agent displaced by the device. In FIG. 7 the syringe outlet was pointed in an upward direction. The end of the catheter connected to the outlet was 2.5" inches higher than the syringe outlet. In FIG. 8 the syringe outlet pointed in a downward direction. The end of the catheter connected to the outlet was 5" higher than the syringe outlet. In FIG. 9, the syringe outlet pointed in a horizontal direction. The end of the catheter connected to the outlet was at the same height as the outlet.

EXAMPLE 6

A gas generating engine was made as follows: In an acrylic sphere, that was ¾ inches in diameter, a 0.173 inch diameter and 0.720 inch length hole was bored in the center of the sphere. 0.70 g of solid composition containing 100% acidic compound and basic compound in a one to one stoichiometric arrangement were compressed into a tubular shaped tablet and placed in the hole. The composition protruded 0.25 inches from the sphere. The acidic compound was citric acid and the basic compound was sodium bicarbonate.

On the opposite side of the sphere in which the hole was bored for the solid composition, two additional holes were bored having a diameter of 0.125 and a length of 0.3 inches. In these holes were inserted two cylindrical lead weights.

The gas generating engine was then placed in a microporous bag (2 mil thick, 3M HDPE Sctoch Pack 9710). 10 cc of water was placed in the bag. The bag was heat sealed and placed in the beneficial agent dispensing device identical to that described in Example 4. The syringe portion of the device contained 140 cc of beneficial agent. The device was tested in a horizontal postion at room temperature. FIG. 10 shows the volume of beneficial agent displaced by the device and the pressure generated by the gas generating engine.

While certain preferred embodiments of the present invention have been selected for illustration in the drawings and have been selected for illustration in the drawings and have been described in detail herein, the illustrated embodiments should not be construed as limiting and those skilled in the art will appreciate that various modifications, changes, additions and omissions to the illustrated embodiments amy be made without departing from the spirit and scope of the present invention as defined in the appended claims.

We claim:

1. A gas generating engine for driving a beneficial agent dispenser that dispenses the beneficial agent at a substantially constant rate over a substantial portion of a predetermined agent administration period, said engine generating gas at a substantially constant rate throughout said predetermined portion of said administration period upon immersion in a material selected from the group consisting of a basic fluid, an acidic fluid and water contained in said dispenser, said engine comprising:

(a) a material selected from the group consisting of, respectively, a solid acidic composition; a solid basic composition and a mixture of solid acidic and basic compositions; and (b) means for maintaining the surface area of said solid composition that is exposed to said fluid in said dispenser substantially constant throughout said predetermined portion of said administration period.

2. The engine of claim 1 further comprising means for generating gas at an initial rate higher than said substantially constant rate, said means comprising a portion of said engine having a surface area exposed to said fluid which is larger than said constant area.

3. The engine of claim 1, wherein the means for maintaining the surface area of the solid composition exposed to the reservoir fluid substantially constant comprises a body surrounding at least 50% of the surface area ofithe solid composition, wherein in operation the body maintains two of the three dimensions of the solid composition constant as the reservoir fluid dissolves the solid composition.

4. The engine of claim 3, wherein the solid composition is tubular in shape and the body which surrounds the composition is tubular in shape.

5. The engine of claim 4, wherein the body surrounds at least 80% of the surface area of the solid composition.

6. The engine of claim 1, wherein the solid composition further comprises a water soluble, inorganic salt.

7. The engine of claim 1, wherein the solid composition comprises:

(i) 50% to 95% of an acidic solid compound, and (ii) 5% to 50% of a water soluble, inorganic salt.

8. The engine of claim 1, wherein the solid composition comprises:

(i) 70% to 90% of an acidic solid compound and (ii) 10% to 30% of a water soluble, inorganic salt.

9. The engine of claim 7, wherein the solid basic composition is $NaHCO_3$ and the acidic compound is $HO(CH_2COOH)_2COOH$.

10. The engine of claim 9, wherein the solid basic compound comprises 90%–100% $NaHCO_3$, 0–10% polyvinyl pyrrolidone and 0–5% magnesium stearate and the reservoir fluid comprises water and 0.01%–10% $HO(CH_2COOH)_2COOH$.

11. A fluid driven dispensing device for delivering an agent into an environment of use at a substantially constant rate over a substantial portion of a predetermined agent administration period, the device comprising:

(a) a syringe having a moveable piston, the piston dividing the syringe into an agent compartment and a driving compartment said agent compartment having outlet means communicating with the environment of use;

(b) a reservoir fluid in said driving compartment and comprising a material selected from the group consisting of an aqueous basic fluid, an aqueous acidic fluid and water; and (c) a gas generating engine disposed within the driving compartment, the gas generating engine comprising:

(i) a material selected from the group consisting of, respectively, a solid acidic composition, a solid basic composition an a mixture of a solid acidic and a solid basic composition; and (ii) means for maintaining the surface area of the solid composition exposed to the reservoir fluid substantially constant over said substantial portion of said administration period; wherein in operation, the agent is delivered from the device by reacting the solid composition with the reservoir fluid to generate a gas in the driving compartment which exerts pressure on the piston to deliver the agent from the agent compartment to the environment of use.

12. The device of claim 11, wherein the means for maintaining substantially constant the surface area of the solid composition exposed to the reservoir fluid comprises a body surrounding at least 50% of the surface area of the solid composition, wherein in operation the body maintains two of the three dimensions of the solid composition constant as the reservoir fluid dissolves the solid composition.

13. The device of claim 12, wherein the solid composition is tubular in shape and the body which surrounds the composition is tubular in shape.

14. The device of claim 12, wherein the solid composition is tubular in shape and the body which surrounds the composition is spherical in shape.

15. The device of claim 11 further comprising means for generating gas at an initial rate higher than said substantially constant rate, said means comprising a portion of said composition having a surface area exposed to said fluid which is larger than said constant area.

16. A fluid driven dispensing device for delivering an agent into an environment of use at a substantially constant rate over a substantial portion of a predetermined agent administration period, the device comprising:

(a) housing means;

(b) piston means slidably received within the housing means, the piston means having first and second ends, the first end having a cross-sectional area greater than the second end;

(c) an agent compartment formed between the housing means and the second end of the piston means and having agent outlet means communicating with the environment of use;

d) a driving compartment formed between the housing means and the second end of the piston means;

(e) a reservoir fluid in said driving compartment and comprising a material selected from the group consisting of an aqueous basic fluid, an aqueous acidic fluid and water; and (f) a gas generating engine within the driving compartment actuateable by the reservoir fluid, the gas generating engine comprising:

(i) a material selected from the group consisting of, respectively, a solid acidic composition, a solid basic composition and a mixture of a solid acidic and a solid basic composition; and (ii) means for maintaining the surface area of the solid composition exposed to the reservoir fluid substantially constant over said substantial portion of said administration period;

whereby a given volume of gas delivered to the driving compartment from the engine means will dispense a larger volume of agent from the agent compartment.

17. The device of claim 16, wherein the means for maintaining substantially constant the surface area of the solid composition exposed to the reservoir fluid comprises a body surrounding at least 50% of the surface area of the solid composition, wherein in operation the body maintains two of the three dimensions of the solid composition constant as the reservoir fluid dissolves the solid composition.

18. The device of claim 17, wherein the solid composition is tubular in shape and the body which surrounds the composition is tubular in shape.

19. The device of claim 17, wherein the solid composition is tubular in shape and the body which surrounds the composition is spherical in shape.

20. The device of claim 16 wherein the area of the first end of the piston is at least 1.5 times greater than the area of the second end.

21. The device of claim 16 wherein the area of said first end is between 3 and 10 times greater than the area of said second end.

22. The device of claim 12 or 16, wherein the solid composition further comprises a water soluble, inorganic salt.

23. The device of claim 12 or 16, wherein the solid composition comprises:

(i) 50% to 95% of an acidic solid compound and basic solid compound, and (ii) 5% to 50% of a water soluble, inorganic salt.

24. The device of claim 12 or 16, wherein the solid composition comprises:

(i) 70% to 90% of an acidic solid compound and basic solid compound, and (ii) 10% to 30% of a water soluble, inorganic salt.

25. The device of claim 12 or 16, wherein the solid composition comprises a basic compound and the reservoir fluid comprises water and an acid compound.

26. The device of claim 12 or 16, wherein the solid composition is $NaHCO_3$ and the reservoir fluid comprises water and $HO(CH_2COOH)_2COOH$.

27. The device of claim 12 or 16, wherein the solid composition comprises 90%–100% $NaHCO_3$, 0–10% polyvinyl pyrrolidone and 0–5% magnesium stearate and the reservoir fluid comprises water and 0.01%–10% $HO(CH_2COOH)_2COOH$.

28. The device of claim 16, further comprising a self-righting means wherein the surface area of the solid composition exposed to the reservoir fluid faces in an upward direction regardless of the orientation of the device.

29. The device of claim 28, wherein the self-righting means comprises one end of the means for maintaining the surface area of the solid composition exposed to the reservoir fluid substantially constant being heavier than the other end of the means.

30. The device of claim 28, wherein the self-righting means comprises an air bubble in one end of the tube.

31. The device of claim 28, wherein the self-righting means comprises a ball on one end of the tube.

32. The device of claim 16 further comprising means for generating gas at an initial rate higher than said substantially constant rate, said means comprising a portion of said composition having a surface area exposed to said fluid which is larger than said constant area.

33. A fluid driven dispensing device for delivering a beneficial agent to an environment of use at a substantially constant rate over a substantial portion of a predetermined agent administration period, the device comprising:

a) a syringe housing adapted to contain the agent and having outlet means proximate one end thereof;

b) an amplication housing attached at one end to the other end of the syringe housing;

c) a driving housing attached to the other end of the amplification housing adapted to contain a reservoir fluid;

d) piston means slidably received within the syringe housing and the amplification housing, the end of the piston means within the syringe housing comprising plunger means having a larger cross-sectional area than the end of the piston proximate the driving housing, the piston means being movable from a first position proximate the amplification housing end of the syringe housing to a second position proximate the outlet means;

e) a reservoir fluid comprising a material selected from the group consisting of an aqueous basic fluid, an aqueous acidic fluid and water within the driving housing; and (f) a gas generating engine within the driving compartment actuateable by the reservoir fluid and in gas communicating relationship with the piston means, the gas generating means comprising:

(i) a material selected from the group consisting of, respectively, a solid acidic composition, a solid basic composition and a mixture of a solid acidic and a solid basic composition; and (ii) means for maintaining the surface area of the sollid composition exposed to the reservoir fluid substantially constant over said substantial portion of said administration period;

whereby a given volume of gas delivered to the piston means from the gas generating engine will dispense a larger volume of an agent from the syringe housing.

34. The device of claim 33, wherein the means for maintaining substantially constant the surface area of the solid composition exposed to the reservoir fluid comprises a body surrounding at least 50% of the surface area of the solid composition, wherein in operation the body maintains two of the three dimensions of the solid composition constant as the reservoir fluid dissolves the solid composition.

35. The device of claim 34, wherein the solid composition is tubular in shape and the body which surrounds the composition is tubular in shape.

36. The device of claim 35, wherein the solid composition is tubular in shape and the body which surrounds the composition is spherical in shape.

37. The device of claim 36 wherein the ratio of the cross-sectional area of the plunger means to the opposite end of the piston means is at least 1.5 to 1.

38. The device of claim 36 wherein the ratio of the cross-sectional area of the plunger means to the opposite end of the piston means is between 3 and 10 to 1.

39. The device of claim 36 further comprising:

g) collapsible enclosure means enclosing the reservoir fluid for the gas generating engine, the enclosure means being disposed within the driving housing; and h) releasing means for puncturing the enclosure means; whereby the reservoir fluid may be released into the driving housing and into contact with the gas generating engine.

40. The device of claim 39 further comprising:

i) means on the driving housing for placing the releasing means in puncturing relationship to the enclosure means.

41. The device of claim 33 further comprising means for generating gas at an initial rate higher than said substantially constant rate, said means comprising a portion of said composition having a surface area exposed to said fluid which is larger than said constant area.

42. In a fluid driven agent dispensing device comprising:

piston means having first and second ends; and housing means slideably receiving the piston means, the first end of the housing forming an agent dispensing compartment having outlet means through which an agent may be displaced by movement of the first end of the piston, the second end of the housing being adapted to maintain a gas generating engine in discharging relationship to the second end of the piston and to contain a reservoir fluid for the engine fluid for the engine; the improvement, whereby the a small volume of gas can dispense a larger volume of agent at a substantially constant rate over a substantial portion of a predetermined administration period, which comprises:

a) the cross-sectional area of the first end of the piston is at least 1.5 times the cross-sectional area of the second end;

b) the reservoir fluid is a material selected from the group consisting of an aqueous basic fluid, an aqueous acidic fluid and water; and c) the gas generating engine comprises:

(i) a material selected from the group consisting of, respectively, a solid acidic composition, a solid basic composition and a mixture of a solid acidic and a solid basic composition; and (ii) means for maintaining the surface area of the solid composition exposed to the reservoir fluid substantially constant over said substantial portion of said administration period.

43. The device of claim 42 further comprising means for generating gas at an initial rate higher than said substantially constant rate, said means comprising a portion of said composition having a surface area exposed to said fluid which is larger than said constant area.

* * * * *

UNITED STATES PATENT AND TRADEMARK OFFICE
CERTIFICATE OF CORRECTION

PATENT NO. : 5,540,665
DATED : July 30, 1996
INVENTOR(S) : Stanley A. Mercado, Mark M. McPhee, Avtar S. Nat, Su Il Yum, Scott A. Bura It is certified that error appears in the above-indentified patent and that said Letters Patent is hereby corrected as shown below:

Claim 3, column 16, line 19, "ofithe" should read --of the--;
Claim 33, column 19, line 18, "sollid" should read --solid--.

Signed and Sealed this

Fifth Day of November, 1996

Attest:

BRUCE LEHMAN

Attesting Officer

Commissioner of Patents and Trademarks